(12) United States Patent
Nakashima et al.

(10) Patent No.: US 9,879,250 B2
(45) Date of Patent: Jan. 30, 2018

(54) PROTEIN-STABILIZING AGENT AND PROTEIN-STABILIZING METHOD

(71) Applicant: NOF CORPORATION, Tokyo (JP)

(72) Inventors: Fumio Nakashima, Kawasaki (JP); Masaru Matsuda, Kawasaki (JP); Tomozumi Noda, Kawasaki (JP); Satoshi Yamada, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/502,387

(22) PCT Filed: Aug. 6, 2015

(86) PCT No.: PCT/JP2015/072328
§ 371 (c)(1),
(2) Date: Feb. 7, 2017

(87) PCT Pub. No.: WO2016/021678
PCT Pub. Date: Feb. 11, 2016

(65) Prior Publication Data
US 2017/0226499 A1 Aug. 10, 2017

(30) Foreign Application Priority Data

Aug. 8, 2014 (JP) ................................ 2014-162111

(51) Int. Cl.
*C12N 9/96* (2006.01)
*C07F 9/10* (2006.01)
*C12N 9/16* (2006.01)

(52) U.S. Cl.
CPC ................. *C12N 9/96* (2013.01); *C07F 9/10* (2013.01); *C12N 9/16* (2013.01); *C12Y 301/03001* (2013.01)

(58) Field of Classification Search
CPC ..................................... C12N 9/96; C07F 9/10
See application file for complete search history.

(56) References Cited

U.S. PATENT DOCUMENTS 8,680,314 B2 * 3/2014 Yoshioka ................ C07F 9/106
558/169
2013/0310591 A1 11/2013 Yoshioka et al.

FOREIGN PATENT DOCUMENTS

| JP | 10-45794 A | 2/1998 |
| JP | 2005-239987 A | 9/2005 |
| JP | 2014-91803 A | 5/2014 |
| WO | 2012/086762 A1 | 6/2012 |

OTHER PUBLICATIONS

International Searching Authority, International Search Report of PCT/JP2015/072328 filed Sep. 8, 2015. [PCT/ISA/210].

* cited by examiner

*Primary Examiner* — Golam M M Shameem
(74) *Attorney, Agent, or Firm* — Sughrue Mion, PLLC

(57) ABSTRACT

There is provided a protein stabilizer containing a compound represented by Formula (1) as an active ingredient. The protein stabilizer is capable of stabilizing a protein in a solution state for a long period of time without affecting an assay system, the protein being not limited to enzymes, labeling substances such as fluorescent substances and chemiluminescent substances, and assay target substances. There is also provided a protein stabilization method containing making the protein coexist with the compound represented by Formula (1) in a water-containing solution.

$$CH_3\text{-}(CH_2)_n\text{-}S\text{-}CH_2\text{-}CH\text{-}\underset{\underset{O}{\|}}{C}\text{-}O\text{-}CH_2\text{-}CH_2\text{-}O\text{-}\underset{\underset{O}{\|}}{P}\text{-}O\text{-}CH_2\text{-}CH_2\text{-}\overset{+}{N}(CH_3)_3 \quad (1)$$

In Formula (1), X is a hydrogen atom or a methyl group, and n is an integer of 3 to 17.

5 Claims, No Drawings

PROTEIN-STABILIZING AGENT AND PROTEIN-STABILIZING METHOD

CROSS REFERENCE TO RELATED APPLICATIONS

This application is a National Stage of International Application No. PCT/JP2015/072328 filed Aug. 6, 2015, claiming priority based on Japanese Patent Application No. 2014-162111, filed Aug. 8, 2014, the contents of all of which are incorporated herein by reference in their entirety.

FIELD OF ART

The present invention relates to a protein stabilizer for stabilizing a protein in a solution state.

BACKGROUND ART

In recent years, assay methods utilizing immune responses, such as enzyme immunoassay methods and chemiluminescent enzyme immunoassay methods, have been widely used in the fields of clinical examinations and diagnostic pharmaceuticals. A system for such a biochemical assay method (hereinafter referred to simply as an assay system) is required to be capable of specifically and accurately detecting a protein derived from various organisms. The protein is used as the assay target and has to remain stable for a long period of time. However, most of proteins are readily denatured or deactivated to lose the bioactivities due to various factors such as temperatures, lights, pHs, salt concentrations, and oxidation factors. Thus, during the storage of the protein, it is important to protect the protein from the external factors to maintain the bioactivity.

Meanwhile, in a commonly known method for retaining an antibody activity, antigenicity, enzymatic activity, or the like of a clinical diagnosis antibody or antigen, a labeled antibody or antigen, or the like in a solution state, frozen state, or freeze-dried state, an additive such as a sucrose, saccharose, or bovine serum albumin (hereinafter referred to as BSA) is added thereto (Non-Patent Literature 1). Furthermore, a method using a particular synthetic polymer for stabilizing a protein is disclosed in Patent Literature 1.

CITATION LIST

Patent Literature 1: JP H10-45794 A
Non-Patent Literature 1: Eiji Ishikawa, "*Koso Men-eki Sokuteiho (Enzyme Immunoassay)*", Igaku-Shoin Ltd., May 1, 1987

SUMMARY OF THE INVENTION

Problems to be Solved by the Invention

However, in the method using the additive described in Non-Patent Literature 1, satisfactory stabilization effects have not been achieved. On the other hand, in the method described in Patent Literature 1, the addition of the polymer results in solution viscosity increase, and the resultant solution is poor in handling disadvantageously.

Accordingly, an object of the present invention is to provide a protein stabilizer capable of stabilizing a protein in a solution state for a long period of time without affecting an assay system, the protein being not limited to enzymes, labeling substances such as fluorescent substances and chemiluminescent substances, and assay target substances.

Means for Solving the Problem

As a result of intense research in view of the above object, the inventors have found that a compound represented by Formula (1) is capable of stabilizing a protein in a water-containing solution. The present invention has been accomplished based on this finding.

According to an aspect of the present invention, there is provided a protein stabilizer comprising, as an active ingredient, a compound represented by following Formula (1):

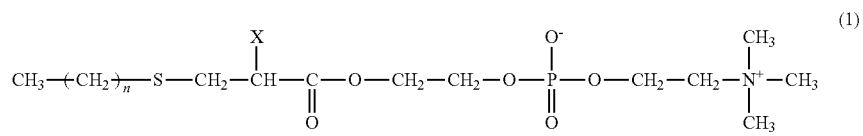

(1)

wherein X is a hydrogen atom or a methyl group and n is an integer of 3 to 17.

The protein stabilizer of the present invention is particularly suitable for stabilizing a protein selected from peroxidases and alkaline phosphatases.

The protein stabilizer of the present invention preferably contains water.

According to another aspect of the present invention, there is provided use of the compound represented by Formula (1) for stabilizing the protein.

According to a further aspect of the present invention, there is provided a method for stabilizing the protein, comprising making the protein coexist with the compound represented by Formula (1) in a water-containing solution.

Effect of the Invention

The compound of Formula (1), which is used as the active ingredient in the protein stabilizer of the present invention, is capable of stabilizing the protein for a long period of time. The activity of the protein can be easily retained merely by making the protein coexist with the compound of Formula (1) in the water-containing solution. A protein stabilization solution, which contains the protein stabilizer and the protein such as a protein of a plasma preparation, a labeled immunoactive substance, or an enzyme, can remain stable for a long time. The protein stabilization solution can be widely used for assay methods utilizing immune responses, such as enzyme immunoassay methods and chemiluminescent enzyme immunoassay methods, in the fields of clinical examinations and diagnostic pharmaceuticals.

EMBODIMENTS OF THE INVENTION

The present invention will be described in detail below. In the following description, the term "protein solution" means a solution in which only a protein is dissolved, the term "protein stabilization solution" means a solution in which a protein and a protein stabilizer according to the present invention are dissolved, and the term "protein stabilizer solution" means a protein stabilizer according to the present invention in the form of a solution containing a compound represented by Formula (1) and water.

In the protein stabilizer of the present invention, the compound represented by Formula (1) is used as an active ingredient. In Formula (1), X is a hydrogen atom or a methyl group, and n is an integer of 3 to 17. It is preferred that n is 7 to 11 from the viewpoint of achieving a higher protein stabilization effect. The substituents on the terminal N atom are methyl groups.

For example, the compound of Formula (1) may be synthesized by reacting 2-methacryloyloxyethyl-2-trimethylammonioethyl phosphate (MPC) and 1-alkanethiol with an amine-based catalyst such as diisopropylamine in an alcohol solvent at room temperature for 10 to 50 hours. The 1-alkanethiol preferably has 4 to 18 carbon atoms.

The protein stabilizer of the present invention preferably contains water. The water is preferably a purified water, a pure water, an ion-exchange water, or the like. The protein stabilizer may be a solution prepared by dissolving the compound of Formula (1) in a buffer containing the water. The buffer may be a known buffer commonly used in this field, as long as it does not act to deteriorate a bioactivity (such as an enzymatic activity or an antigenicity) of the protein. Examples of such buffers include phosphate buffers, Tris buffers, Good buffers, glycine buffers, borate buffers, and mixtures thereof. The solution may be referred to as the protein stabilizer solution as described above.

In the protein stabilizer solution, the content of the compound represented by Formula (1) is preferably 0.01% by mass or more, more preferably 0.1% by mass or more. The upper limit of the content is not particularly limited as long as the compound can be dissolved in the main solvent of water. The content is for example 20% by mass or less, preferably 10% by mass or less. When the content is within the range, the protein stabilizer solution can exhibit a high protein stabilization effect. Furthermore, the dissolution of the protein in the protein stabilizer solution or the mixing of the protein solution with the protein stabilizer solution can be satisfactorily performed.

Specific examples of the compounds represented by Formula (1) include 2-[3-(butylsulfanyl)-2-methylpropionyloxy]ethyl-2-(trimethylammonio)ethyl phosphate (X is a methyl group and n is 3 in Formula (1)), 2-[3-(hexylsulfanyl)-2-methylpropionyloxy]ethyl-2-(trimethylammonio) ethyl phosphate (X is a methyl group and n is 5 in Formula (1)), 2-[3-(octylsulfanyl)-2-methylpropionyloxy]ethyl-2-(trimethylammonio)ethyl phosphate (X is a methyl group and n is 7 in Formula (1)), 2-[3-(decylsulfanyl)-2-methylpropionyloxy]ethyl-2-(trimethylammonio)ethyl phosphate (X is a methyl group and n is 9 in Formula (1)), 2-[3-(dodecylsulfanyl)-2-methylpropionyloxy]ethyl-2-(trimethylammonio)ethyl phosphate (X is a methyl group and n is 11 in Formula (1)), 2-[3-(tetradecylsulfanyl)-2-methylpropionyloxy]ethyl-2-(trimethylammonio)ethyl phosphate (X is a methyl group and n is 13 in Formula (1)), 2-[3-(hexadecylsulfanyl)-2-methylpropionyloxy]ethyl-2-(trimethylammonio)ethyl phosphate (X is a methyl group and n is 15 in Formula (1)), and 2-[3-(octadecylsulfanyl)-2-methylpropionyloxy]ethyl-2-(trimethylammonio)ethyl phosphate (X is a methyl group and n is 17 in Formula (1)).

In addition to the compound of Formula (1), the protein stabilizer may further contain a known compound commonly used for stabilizing the protein in this field. Examples of such compounds include saccharides, proteins other than the protein to be stabilized, salts and the like, and surfactants. Examples of the saccharides include lactose, sucrose, and trehalose. Examples of the proteins include bovine serum albumins, gelatins, and caseins. Examples of the salts and the like include amino acids such as glycine, alanine, serine, threonine, glutamic acid, aspartic acid, glutamine, asparagine, lysine, and histidine, salts of the amino acids, peptides such as glycylglycine, inorganic salts such as phosphates, borates, sulfates, and Tris salts, organic acids such as flavins, acetic acid, citric acid, malic acid, maleic acid, and gluconic acid, and salts of the organic acids. Examples of the surfactants include polyoxyethylene alkyl ethers.

A method for using the protein stabilizer of the present invention will be described below.

The protein, which is stabilized by the protein stabilizer of the present invention, is not particularly limited. Examples of the proteins include acetylcholinesterases, alkaline phosphatases, β-D-galactosidases, glucoamylases, glucose oxidases, glucose-6-phosphate dehydrogenases, hexokinases, penicillinases, peroxidases, and lysozymes. Preferred examples of the proteins include peroxidases and alkaline phosphatases commonly used in enzyme immunoassay methods.

The protein may be dissolved in a solvent to prepare the protein solution before the stabilization according to the present invention. The solvent may be a known buffer commonly used in this field, as long as it does not act to deteriorate a bioactivity (such as an enzymatic activity or an antigenicity) of the protein. Examples of such buffers include phosphate buffers, Tris buffers, Good buffers, glycine buffers, borate buffers, and mixtures thereof.

For example, the protein stabilizer of the present invention may be used for stabilizing the protein in an assay system utilizing an antibody or the like labeled with the protein.

The protein stabilizer of the present invention may be added to the protein solution to perform the stabilization. Alternatively, the protein stabilizer may be prepared in the form of the protein stabilizer solution, and the stabilization target protein may be dissolved in the protein stabilizer solution. Alternatively, the protein solution and the protein stabilizer solution may be prepared separately and then mixed with each other.

In any case, in the protein stabilization solution containing both of the protein and the protein stabilizer, the concentration of the compound represented by Formula (1) is preferably 0.01% to 10% by mass, more preferably 0.01% to 0.1% by mass. When the concentration is less than 0.01% by mass, the protein stabilization solution may have an insufficient protein stabilization effect. When the concentration is more than 10% by mass, the solution may be easily bubbled and cannot be easily handled.

In the stabilization of the protein by the protein stabilizer of the present invention, the protein stabilization solution is preferably maintained at a temperature of 2° C. to 40° C. When the temperature is 2° C. or lower, the protein stabilization solution may be frozen. When the temperature is 40° C. or higher, the protein can be stabilized only over a limited period.

The protein stabilization solution may further contain another compound. The compound may be a compound commonly used for stabilizing the protein in this field. Examples of the compounds include the above described compounds for the protein stabilizer.

EXAMPLES

The present invention will be described more specifically below with reference to Examples without intention of restricting the invention. In Examples, compounds of Formula (1) prepared in Synthesis Examples were used as active ingredients in protein stabilizers.

Synthesis of Compound Represented by Formula (1)

Synthesis Example 1

14.7635 g (0.050 mol) of 2-methacryloyloxyethyl-2-trimethylammonioethyl phosphate and 4.9605 g (0.055 mol) of 1-butanethiol were dissolved in 81.00 g of ethanol (EtOH). To this was added 0.2226 g (0.0022 mol) of diisopropylamine as a catalyst, and the compounds were reacted at the room temperature for 24 hours. After the reaction, the reaction liquid was concentrated, and the residue was reprecipitated with ethyl acetate to produce a white powder of the compound represented by Formula (1) (wherein X is a methyl group and n is 3).

Synthesis Example 2

A white powder of the compound represented by Formula (1), 2-[3-(octylsulfanyl)-2-methylpropionyloxy]ethyl-2-(trimethylammonio)ethyl phosphate (X is a methyl group and n is 7 in the Formula (1)), was produced in the same manner as Synthesis Example 1 except that 1-octanethiol was used instead of 1-butanethiol, and the amount was controlled to obtain the same molar ratio as Synthesis Example 1.

Synthesis Example 3

A white powder of the compound represented by Formula (1), 2-[3-(decylsulfanyl)-2-methylpropionyloxy]ethyl-2-(trimethylammonio)ethyl phosphate (X is a methyl group and n is 9 in the Formula (1)), was produced in the same manner as Synthesis Example 1 except that 1-decanethiol was used instead of 1-butanethiol, and the amount was controlled to obtain the same molar ratio as Synthesis Example 1.

Synthesis Example 4

A white powder of the compound represented by Formula (1), 2-[3-(dodecylsulfanyl)-2-methylpropionyloxy]ethyl-2-(trimethylammonio)ethyl phosphate (X is a methyl group and n is 11 in the Formula (1)), was produced in the same manner as Synthesis Example 1 except that 1-dodecanethiol was used instead of 1-butanethiol, and the amount was controlled to obtain the same molar ratio as Synthesis Example 1.

Synthesis Example 5

A white powder of the compound represented by Formula (1), 2-[3-(tetradecylsulfanyl)-2-methylpropionyloxy]ethyl-2-(trimethylammonio)ethyl phosphate (X is a methyl group and n is 13 in the Formula (1)), was produced in the same manner as Synthesis Example 1 except that 1-tetradecanethiol was used instead of 1-butanethiol, and the amount was controlled to obtain the same molar ratio as Synthesis Example 1.

Comparative Synthesis Example 1

A compound, which had a structure corresponding to Formula (1) but the value of n was outside the range of Formula (1), was synthesized as follows. A white powder of the compound, 2-[3-(eicosasulfanyl)-2-methylpropionyloxy]ethyl-2-(trimethylammonio)ethyl phosphate (X is a methyl group and n is 19 in the Formula (1)), was produced in the same manner as Synthesis Example 1 except that 1-eicosanethiol was used instead of 1-butanethiol, and the amount was controlled to obtain the same molar ratio as Synthesis Example 1.

Example 1-1: Examples 1-1-1 and 1-1-2

<Preparation of Protein Stabilizer Solution>

Two protein stabilizer solutions were prepared by dissolving the compound produced in Synthesis Example 1 in a phosphate buffer (pH 7.4) in such a manner that the final concentrations were controlled at 1.000% by mass (Example 1-1-1) and 0.100% by mass (Example 1-1-2) shown in Table 1 respectively.

<Evaluation of Protein Stabilization Effect>

A phosphate buffer (pH 7.4) containing a peroxidase-labeled antimouse IgG goat antibody was dissolved at a concentration of 0.5% by mass in each of the above protein stabilizer solutions to prepare a protein stabilization solution. The protein stabilization solution was incubated at 4° C. for days shown in Table 1. After the incubation, the protein stabilization solution was added to a polystyrene 96-well plate at 8 μL/well. A 0.01% by mass citrate buffer (pH 4.0) containing 3,3',5,5'-tetramethylbenzidine was added thereto at 100 μL/well, so that a chromogenic reaction of the protein was carried out for 5 minutes. Then, a 2-N sulfuric acid was added to the resultant at 50 μL/well to stop the chromogenic reaction. The absorbance of the resulting solution was measured with respect to a light having a wavelength of 450 nm, to evaluate the effect of stabilizing the peroxidase-labeled antimouse IgG goat antibody.

Specifically, the absorbance values were measured by the following method immediately after the preparation of the protein stabilization solution and after the incubation for the days. The enzymatic activity retention rates (%) of each example were calculated using following Mathematical Formula (1). The protein stabilization effect was evaluated based on the enzymatic activity retention rates (%). A higher enzymatic activity retention rate corresponds to a higher protein stabilization effect. The evaluation results are shown in Table 1.

<Absorbance Measurement Method>

The absorbance values of each protein stabilization solution were measured by using the following measurement device under the following measurement condition.

Measurement device: SPECTRA MAX M3 (available from Molecular Devices)

Measurement condition: Endpoint wavelength of 450 or 405 nm

The enzymatic activity retention rates (%) were calculated from the measured absorbance values using following Mathematical Formula (1):

$$\text{Enzymatic activity retention rate (\%)} = \frac{\text{Absorbance value of protein stabilization solution after days of incubation}}{\text{Absorbance value of protein stabilization solution immediately after preparation}} \times 100 \quad (1)$$

Example 1-2: Examples 1-2-1 and 1-2-2

Protein stabilization solutions were prepared in the same manner as Example 1-1 except that the compound produced in Synthesis Example 2 was used instead of the compound produced in Synthesis Example 1 at the concentrations shown in Table 1 respectively. The protein stabilization effects of the protein stabilization solutions were evaluated in the same manner as Example 1-1. The results are shown in Table 1.

Example 1-3: Examples 1-3-1 to 1-3-3

Protein stabilization solutions were prepared in the same manner as Example 1-1 except that the compound produced in Synthesis Example 3 was used instead of the compound produced in Synthesis Example 1 at the concentrations shown in Table 1 respectively. The protein stabilization effects of the protein stabilization solutions were evaluated in the same manner as Example 1-1. The results are shown in Table 1.

Example 1-4: Examples 1-4-1 to 1-4-3

Protein stabilization solutions were prepared in the same manner as Example 1-1 except that the compound produced in Synthesis Example 4 was used instead of the compound produced in Synthesis Example 1 at the concentrations shown in Table 1 respectively. The protein stabilization effects of the protein stabilization solutions were evaluated in the same manner as Example 1-1. The results are shown in Table 1.

Example 1-5: Examples 1-5-1 to 1-5-3

Protein stabilization solutions were prepared in the same manner as Example 1-1 except that the compound produced in Synthesis Example 5 was used instead of the compound produced in Synthesis Example 1 at the concentrations shown in Table 1 respectively. The protein stabilization effects of the protein stabilization solutions were evaluated in the same manner as Example 1-1. The results are shown in Table 1.

Comparative Example 1-1

The protein stabilization effect of Comparative Example 1-1 was evaluated in the same manner as Example 1-1 except that the protein stabilizer was not used and only the phosphate buffer (pH 7.4) was used. The results are shown in Table 1.

Comparative Example 1-2

The protein stabilization effect of Comparative Example 1-2 was evaluated in the same manner as Example 1-1 except that polyoxyethylene sorbitan monolaurate was used as a protein stabilizer, and the protein stabilization solution was prepared in such a manner that the final concentration was controlled at 0.5% by mass. The results are shown in Table 1.

Comparative Example 1-3

Preparation of a protein stabilization solution was tested in the same manner as Example 1-1 except for using the compound produced in Comparative Synthesis Example 1. However, the compound produced in Comparative Synthesis Example 1 was not dissolved in the phosphate buffer, so that the protein stabilization effect could not evaluated.

TABLE 1

| | Active ingredient | | Enzymatic activity retention rate (%) | | | |
|---|---|---|---|---|---|---|
| | Syn. Ex. | Concentration (% by mass) *1 | Initial | 7 days after | 14 days after | 30 days after |
| Ex. 1-1 -1 | 1 | 1.000 | 100 | 87 | 20 | 7 |
| -2 | | 0.100 | 100 | 30 | 21 | 14 |
| Ex. 1-2 -1 | 2 | 0.100 | 100 | 65 | 50 | 34 |
| -2 | | 0.010 | 100 | 54 | 49 | 38 |
| Ex. 1-3 -1 | 3 | 0.100 | 100 | 67 | 61 | 47 |
| -2 | | 0.010 | 100 | 89 | 80 | 75 |
| -3 | | 0.001 | 100 | 42 | 41 | 30 |
| Ex. 1-4 -1 | 4 | 0.100 | 100 | 68 | 49 | 17 |
| -2 | | 0.010 | 100 | 84 | 78 | 65 |
| -3 | | 0.001 | 100 | 72 | 73 | 57 |
| Ex. 1-5 -1 | 5 | 0.100 | 100 | 71 | 58 | 42 |
| -2 | | 0.010 | 100 | 80 | 74 | 73 |
| -3 | | 0.001 | 100 | 73 | 77 | 57 |
| Comp. Ex. 1-1 | — | — | 100 | 5 | 5 | 5 |
| Comp. Ex. 1-2 | *2 | 0.500 | 100 | 30 | 13 | 5 |
| Comp. Ex. 1-3 | Comp. Syn. Ex. 1 | — | | Unevaluable | | |

*1: Concentration in protein stabilization solution
*2: Polyoxyethylene sorbitan monolaurate As is clear from Table 1, the protein (peroxidase) is stabilized more highly by the protein stabilizers of Examples 1-1 to 1-5 using the compounds according to the present invention than by the solutions of Comparative Examples. Incidentally, the enzymatic activity retention rate is slightly increased with incubation time in some cases. This increase is considered as a measurement error.

Example 2-1

<Preparation of Protein Stabilizer Solution>

The compound produced in Synthesis Example 1 was dissolved in a Tris buffer (pH 8.0) to prepare a protein stabilizer solution having a final concentration twice the value shown in Table 2.

<Evaluation of Protein Stabilization Effect>

(1) The prepared protein stabilizer solution was mixed with the same amount of a protein solution containing an alkaline phosphatase, sucrose, and $MgCl_2$ in a Tris buffer (pH 8.0), to prepare a protein stabilization solution. In the protein solution, the concentration of the alkaline phosphatase was 0.2 mg/mL, the concentration of the sucrose was 20% by mass, and the concentration of the $MgCl_2$ was 2 mM.

Therefore, the protein stabilization solution contained 0.1 mg/mL of the alkaline phosphatase. In the protein stabilization solution, the concentration of the compound produced in Synthesis Example 1 was 1.000% by mass as shown in Table 2.

(2) The protein stabilization solution was incubated at 25° C. for days shown in Table 2. After the incubation, the protein stabilization solution was added to a polystyrene 96-well plate at 8 μL/well. 1-STEP PNPP (available from Thermofisher Scientific) was added thereto at 100 μL/well, so that a chromogenic reaction of the protein was carried out for 7 minutes. Then, a 2-N sodium hydroxide solution was added to the resultant at 50 μL/well to stop the chromogenic reaction. The absorbance of the resulting solution was measured with respect to a light having a wavelength of 405 nm, to evaluate the effect of stabilizing the alkaline phosphatase. The absorbance values were measured in the same manner as above except for using the wavelength of 405 nm. The protein stabilization effect was evaluated based on the enzymatic activity retention rates (%) calculated using Mathematical Formula (1) described above. A higher enzymatic activity retention rate corresponds to a higher protein stabilization effect. The evaluation results are shown in Table 2.

Examples 2-2 to 2-5

Protein stabilization solutions were prepared in the same manner as Example 2-1 except that the compounds produced in Synthesis Examples 2 to 5 were used instead of the compound produced in Synthesis Example 1 at the concentrations shown in Table 2 respectively. The protein stabilization effects of the examples were evaluated in the same manner as Example 2-1. The results are shown in Table 2.

Comparative Example 2-1

The protein stabilization effect of Comparative Example 2-1 was evaluated in the same manner as Example 2-1 except that only a Tris buffer (pH 8.0) was used instead of the protein stabilizer solution, and sucrose was not added to the protein solution. The results are shown in Table 2.

Comparative Example 2-2

The protein stabilization effect of Comparative Example 2-2 was evaluated in the same manner as Example 2-1 except that only a Tris buffer (pH 8.0) was used instead of the protein stabilizer solution. The results are shown in Table 2.

TABLE 2

| Active ingredient | | Enzymatic activity retention rate (%) | | | |
|---|---|---|---|---|---|
| Syn. Ex. | Concentration (% by mass) *1 | Initial | 7 days after | 14 days after | 30 days after |
| Ex. 2-1 | 1 | 1.000 | 100 | 94 | 97 | 104 |
| Ex. 2-2 | 2 | 0.100 | 100 | 85 | 75 | 93 |
| Ex. 2-3 | 3 | 0.005 | 100 | 108 | 101 | 98 |
| Ex. 2-4 | 4 | 0.010 | 100 | 101 | 86 | 95 |

TABLE 2-continued

| Active ingredient | | Enzymatic activity retention rate (%) | | | |
|---|---|---|---|---|---|
| Syn. Ex. | Concentration (% by mass) *1 | Initial | 7 days after | 14 days after | 30 days after |
| Ex. 2-5 | 5 | 0.001 | 100 | 88 | 124 | 84 |
| Comp. Ex. 2-1 | — | — | 100 | 21 | 19 | 22 |
| Comp. Ex. 2-2 | — | — | 100 | 66 | 59 | 43 |

*1: Concentration in protein stabilization solution

As is clear from Table 2, the protein (alkaline phosphatase) is stabilized more highly by the protein stabilizers of Examples 2-1 to 2-5 using the compounds according to the present invention than by the solutions of Comparative Examples. Incidentally, the enzymatic activity retention rate is slightly increased with incubation time in some cases. This increase is considered as a measurement error.

What is claimed is:

1. A protein stabilizer comprising, as an active ingredient, a compound represented by following Formula (1):

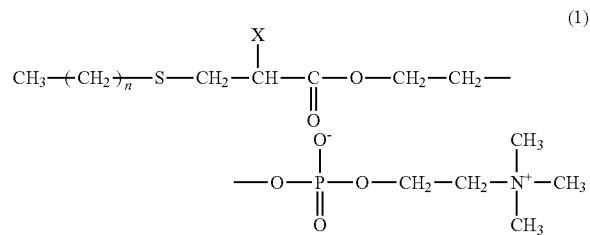

wherein X is a hydrogen atom or a methyl group and n is an integer of 3 to 17.

2. The protein stabilizer according to claim 1, further comprising water.

3. The protein stabilizer according to claim 1, for stabilizing at least one protein selected from peroxidases and alkaline phosphatases.

4. A method for stabilizing a protein, comprising making the protein coexist in a water-containing solution with the compound according to claim 1.

5. The protein stabilizer according to claim 2, for stabilizing at least one protein selected from peroxidases and alkaline phosphatases.

* * * * *